Jan. 19, 1960 D. H. MOREY, JR Plant Pat. 1,899
ROSE PLANT
Filed May 13, 1959
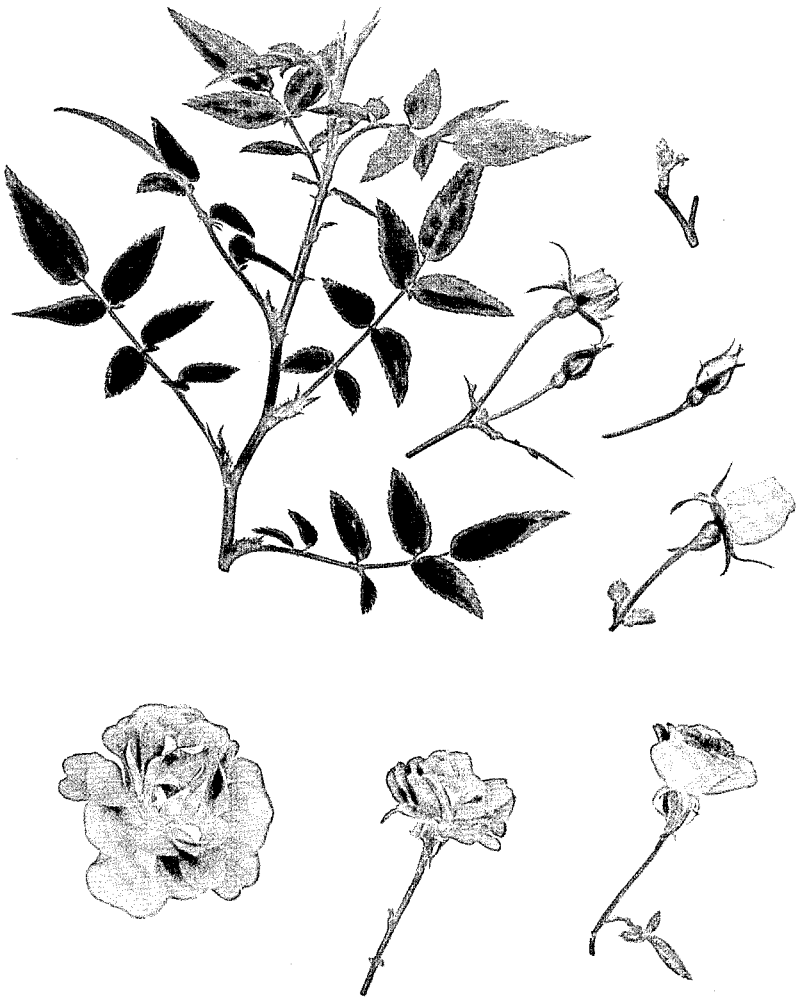
Inventor
D. H. Morey, Jr
By: Robert Cobb
Attorneys United States Patent Office Plant Pat. 1,899
Patented Jan. 19, 1960

1,899

ROSE PLANT

Dennison H. Morey, Jr., Pleasanton, Calif., assignor to Jackson & Perkins Company, Newark, N.Y., a corporation of New York Application May 13, 1959, Serial No. 813,048

1 Claim. (Cl. 47—61)

The present invention relates to a new and distinct variety of rose plant of the miniature class, which was originated by me by crossing an unnamed and unpatented sport of "Dick Koster" (unpatented) with the variety "Tom Thumb" (Plant Patent No. 169), said latter variety also being known in Europe as "Peon."

The primary objective of this breeding was to produce a miniature rose which bears flowers of a new color. This objective was fully achieved, along with other desirable improvements, as evidenced by the following unique combination of characteristics which are outstanding in the new variety and which distinguish it from its parents, as well as from all other varieties of which I am aware:

(1) Ease of propagation by rooted cuttings;

(2) Compact flower heads, with the flowers being much larger than those normally found in miniature roses;

(3) A distinctive irregular arrangement of the flower petals;

(4) An almost silvery appearance of the buds as attributed to the White color of the reverse sides of the petals; and (5) A distinctive Tyrian Rose, lightly overcast with Spinel Red, general color tonality of the flowers, with White at the base and hinge of the petals, which is unusual in miniature roses.

Asexual reproduction of the new variety by own-rooted cuttings, as performed at Pleasanton, California and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed sport of "Dick Koster."

*Pollen parent.*—"Tom Thumb" (known in Europe as "Peon").

Classification:

*Botanic.*—Hybrid chinensis minima.

*Commercial.*—Miniature.

*Flower*

(Observations made from specimens grown in a greenhouse at Newark, New York in the early morning and during the middle of December.)

Blooming habit: Recurrent—continuous.

Bud:

*Size.*—Small.

*Form.*—Ovoid; is not affected by wet or hot weather.

*Color.*—When sepals first divide—Tyrian Rose, Plate 12. When petals begin to unfurl—White, Plate 53, lightly overcast with Rosolane Pink, Plate 26, with outer edge of petals Rose color, Plate 12. When half-blown: inside of petals—Pomegranate Purple, Plate 12, lightly overcast with Spinel Red, Plate 12; reverse of petals—White, Plate 53, with edges lightly overcast with Light Rosolane Purple, Plate 26.

*Sepals.*—Slightly branched; curl back when petals begin to unfurl. Color: inside—Light Cress Green, Plate 31.

*Calyx.*—Color—Cress Green, Plate 31. Shape—apple. Size—small. Aspect—smooth. Odor when rubbed—none.

*Peduncle.* — Length — short. Aspect — smooth. Strength—erect; slender. Color—Biscay Green, Plate 17.

*Opening.*—Opens up well; is not affected by adverse weather conditions.

Bloom:

*Size.*—Small. Average size when fully expanded—from 1 inch to 1¼ inches.

*Borne.*—Several together and in irregular clusters; compact heads.

*Stems.*—Short; normal strength.

*Form (when first open).*—Open. Permanence—retains its form to the end.

*Petalage.*—Double (full but open center). Number of petals under normal conditions—25.

*Color.*—Center of flower—Indian Lake, Plate 26, lightly overcast with Spinel Red, Plate 26, with lower part of petals White, Plate 53. Outer petals—Spinel Red, Plate 26. Hinge and base of petals (aiglet)—White, Plate 53. Inside of petals—Tyrian Rose, Plate 12, lightly overcast with Spinel Red, Plate 26, with lower part of petal White, Plate 53. Reverse of petals—Pale Rosolane Purple, Plate 26, with outer edge of petal lightly overcast with Light Rosolane Purple, Plate 26, and with lower half of petal White, Plate 53. General tonality from a distance—Spinel Red, Plate 26.

*Discoloration.*—General tonality at end of first day—Tyrian Rose, Plate 12, lightly overcast with Spinel Red, Plate 26. Second day—Spinel Red, Plate 26. Third day—Spinel Red, Plate 26, lightly overcast with Rosolane Purple, Plate 26.

Petals:

*Texture.*—Thin; is not affected by wet or hot weather.

*Appearance.*—Inside—satiny. Outside—shiny.

*Form.*—Oval.

*Arrangement.*—Irregular.

*Petaloids in center.*—Few; small.

*Persistence.*—Drop off cleanly.

*Fragrance.*—Moderate. Nature—tea (average hybrid tea scent).

*Lasting quality.*—On the plant—long. As cut flower—long.

*Genital Organs*

Stamens, anthers: Small; few; regularly arranged around styles. Color—Mustard Yellow, Plate 16.

Stamens, filaments (threads): Short. Color—Light Chalcedony-Yellow, Plate 17.

Pollen: Color—Cream Color, Plate 16.

Styles: Columnar; uneven length; short; thin.

Stigmas: Color—Massicot Yellow, Plate 16.

Ovaries: All enclosed in calyx.

Hips: None.

Seeds: None.

*Plant*

Form: Bush; from 6 inches to 8 inches in height.
Growth: Medium; dwarf; low; compact.
Foliage: Compound of 5 to 7 leaflets.
*Size.*—Small.
*Quantity.*—Abundant.
*Color.*—New foliage:—upper side—Light Cress Green, Plate 31. Under side—Kildare Green, Plate 31. Old foliage:—upper side—Yew Green, Plate 31; Under side—Light Hellebore Green, Plate 17.
*Shape.*—Oval pointed.
*Texture.*—Upper side—glossy. Under side—smooth.
*Ribs and veins.*—Ordinary.
*Edge.*—Serrated (saw-toothed).
*Serration.*—Single; small.
*Leaf stem.*—Color—Jade Green, Plate 31. Under side—smooth.
*Stipules.*—Short; serrated.
Wood:
*New wood.*—Color—Cress Green, Plate 31. Bark—smooth.
*Old wood.*—Color—Dark Cress Green, Plate 31. Bark—smooth.

Thorns:
*Thorns.*—Quantity: on main stalks from base—few; on laterals from stalk—few. Form—narrow base; short. Color (when young)—Alizarine Pink, Plate 13. Position—irregular.
*Prickles.*—Quantity: on main stalks—none; on laterals—none.
*Short needles.*—Quantity: on main stalks—none; on laterals—none.

I claim:

A new and distinct variety of rose plant of the miniature class, substantially as herein shown and described, characterized particularly as to novelty by the unique combination of ease of propagation by rooted cuttings, compact flower heads and unusual large size of the flowers, an unusual irregular arrangement of the flower petals, a distinctive silvery appearance of the buds as attributed to the White color on the reverse of the petals, and a distinctive Tyrian Rose lightly overcast with Spinel Red, general color tonality of the flowers, with an unusual White color at the base and hinge of the flower petals.

No references cited.